United States Patent
Rosines (10) Patent No.: US 11,318,228 B2
(45) Date of Patent: *May 3, 2022

(54) CROSSLINKED SOFT TISSUE GRAFT AND METHODS OF USE THEREOF

(71) Applicant: LifeNet Health, Virginia Beach, VA (US)

(72) Inventor: Eran Rosines, Virginia Beach, VA (US)

(73) Assignee: LifeNet Health, Virginia Beach, VA (US)

(*) Notice: Subject to any disclaimer, the term of this patent is extended or adjusted under 35 U.S.C. 154(b) by 98 days.

This patent is subject to a terminal disclaimer.

(21) Appl. No.: 16/774,672

(22) Filed: Jan. 28, 2020

(65) Prior Publication Data
US 2020/0306412 A1    Oct. 1, 2020

Related U.S. Application Data

(63) Continuation of application No. 14/776,142, filed as application No. PCT/US2014/025870 on Mar. 13, 2014, now Pat. No. 10,561,762.

(60) Provisional application No. 61/784,990, filed on Mar. 14, 2013.

(51) Int. Cl.
A61L 27/36    (2006.01)

(52) U.S. Cl.
CPC ......... *A61L 27/3695* (2013.01); *A61L 27/362* (2013.01); *A61L 27/3604* (2013.01); *A61L 27/3687* (2013.01)

(58) Field of Classification Search
None
See application file for complete search history.

(56) References Cited

U.S. PATENT DOCUMENTS

| | | | |
|---|---|---|---|
| 4,597,762 | A | 7/1986 | Walter et al. |
| 6,117,979 | A | 9/2000 | Hendriks et al. |
| 7,824,447 | B2 | 11/2010 | Xu |
| 10,016,528 | B2 | 7/2018 | Rosines |
| 2006/0100138 | A1 | 5/2006 | Olsen et al. |
| 2010/0030340 | A1 | 2/2010 | Wolfinbarger et al. |
| 2011/0077737 | A1 | 3/2011 | Stroumpoulis et al. |
| 2012/0077272 | A1 | 3/2012 | Kharazi et al. |
| 2012/0165264 | A1 | 6/2012 | Malessa et al. |
| 2013/0029915 | A1 | 1/2013 | Mezger et al. |

OTHER PUBLICATIONS

International Search Report and Written Opinion for International Application No. PCT/US2014/025870, dated Jul. 21, 2014, 8 pages.
Zeeman et al., "Successive Epoxy and Carbodiimide Cross-linking of Dermal Sheep Collagen" Biomaterials, 20, (1999), pp. 921-931.

*Primary Examiner* — David W Berke-Schlessel
(74) *Attorney, Agent, or Firm* — RatnerPrestia

(57) ABSTRACT

The invention relates to crosslinked soft tissue grafts and methods of use thereof. The invention also relates to methods of preparing the same.

20 Claims, 13 Drawing Sheets

Crosslinking (Stabilization) Process

3 Step Process:
1. Incubate tissue with crosslinking agent (1.2% BDDE)

2. Remove free crosslinking agent

3. Incubate sample in buffer to remove free epoxide groups

Crosslinking (Stabilization) Process

3 Step Process:
1. Incubate tissue with crosslinking agent (1.2% BDDE)

2. Remove free crosslinking agent

3. Incubate sample in buffer to remove free epoxide groups

Figure 3

Degree of Crosslinking (1)

Measure amine groups to determine degree of crosslinking

| Hours | Amines (nmol/mgDW) |
|---|---|
| 23 | 157.498 |
| 24 | 154.7804 |
| 25 | 152.1106 |

- Theoretical 285 – 295nmol amine / mg dry weight for dermis tissue (matches 0hr crosslinking)

Figure 4

Degree of Crosslinking (2)

Measure amine groups to determine degree of crosslinking in Step 3

Figure 5

Functional Correlation

Functional result of crosslinking is *collagenase resistance*

- Expected Result:

Amine $\downarrow$ = crosslinking $\uparrow$ = collagenase resistance $\uparrow$

| Hours | Amines (nmol/mgDW) | Collagenase Resistance |
|---|---|---|
| 23 | 157.498 | 76.4 |
| 24 | 154.7804 | 82.0 |
| 25 | 152.1106 | 86.0 |

Stability of Stabilizied Dermis in Response to 20U/mL Collagenase (37C) over Time Control (non-stabilized DermACELL)

Stabilized

CROSSLINKED SOFT TISSUE GRAFT AND METHODS OF USE THEREOF

CROSS-REFERENCE TO RELATED APPLICATIONS

This is a Continuation Application of U.S. application Ser. No. 14/776,142, filed Sep. 14, 2015, allowed, which is the national phase of International Application No. PCT/US2014/025870, filed Mar. 13, 2014, which claims the benefit of priority to Provisional Application No. 61/784,990, filed Mar. 14, 2013. The disclosure of each of these applications is incorporated herein by reference in its entirety for all purposes.

BACKGROUND OF THE INVENTION

The invention relates to crosslinked soft tissue grafts and methods of use thereof. The invention also relates to methods of preparing the same.

SUMMARY

The invention relates to crosslinked soft tissue grafts. The crosslinked soft tissue grafts of some embodiments are resistant to enzymatic degradation and stretching under tension. Further, the cellular infiltration is maintained after implantation of the crosslinked soft tissue grafts of some embodiments.

The invention also relates to methods of preparing a crosslinked soft tissue graft. In some embodiments, the methods of preparing a crosslinked soft tissue graft comprise selecting a soft tissue graft, optionally decellularizing said soft tissue graft, incubating the soft tissue graft with the crosslinking agent, removing the crosslinking agent after the incubation period, optionally rinsing the crosslinked soft tissue in a buffer without the crosslinking agent, optionally treating the cross-linked soft tissue graft with a plasticizer, optionally packaging the cross-linked soft tissue graft, and optionally sterilizing the crosslinked soft tissue graft.

The invention also relates to methods of repairing a soft tissue defect. In some embodiments, the methods of repairing a soft tissue defect comprise obtaining a cross-linked soft tissue graft as described herein, and implanting the crosslinked soft tissue graft into the soft tissue defect site of a subject in need thereof.

DETAILED DESCRIPTION OF THE INVENTION

The invention relates to crosslinked soft tissue grafts. The crosslinked soft tissue grafts of some embodiments are resistant to enzymatic degradation and stretching under tension. Further, the cellular infiltration may be maintained after implantation of the crosslinked soft tissue grafts described herein.

In one aspect, the crosslinked soft tissue grafts provide enzymatic resistance while not inhibiting the natural ability of soft tissue to support cellular infiltration. For example, the crosslinked soft tissue grafts of some embodiments comprise flexible bridges and links that maintain large pore sizes for cells to migrate through (compared to other direct or "zero-length" crosslinks). The crosslinked soft tissue grafts of some embodiments comprise a biocompatible amine bond (rather than isourea or other less biocompatible bond). The crosslinked soft tissue grafts of some embodiments comprise a proper number of bridges or links specifically designed to reduces the possibility of "over crosslinking." On contrary, introducing too many bridges or links may result in that the graft appears to the host as a foreign material, eliciting an inflammatory response. Moreover, too many bonds may prevent cell infiltration and/or remodeling of the soft tissue graft by a host tissue.

In one aspect, the soft tissue graft described herein is crosslinked in a degree from about 10% to about 50%, from about 20% to about 50%, from about 30% to about 50%, from about 40% to about 50%, from about 20% to about 60%, from about 30% to about 60%, from about 40% to about 60%, from about 50% to about 60%, from about 20% to about 70%, from about 20% to about 80%, or from about 20% to about 90%. In some embodiments, the soft tissue graft described herein is crosslinked in a degree of about 5%, 15%, 25%, 35%, 45%, 55%, 65%, 75%, 85%, 95% or less. In some embodiments, the soft tissue graft described herein is crosslinked in a degree of about 3%, 13%, 23%, 33%, 43%, 53%, 63%, 73%, 83%, 93% or more.

As used herein, the term "about" modifying, for example, the quantity of an ingredient in a composition, concentrations, volumes, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent variation in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

Figure 1:
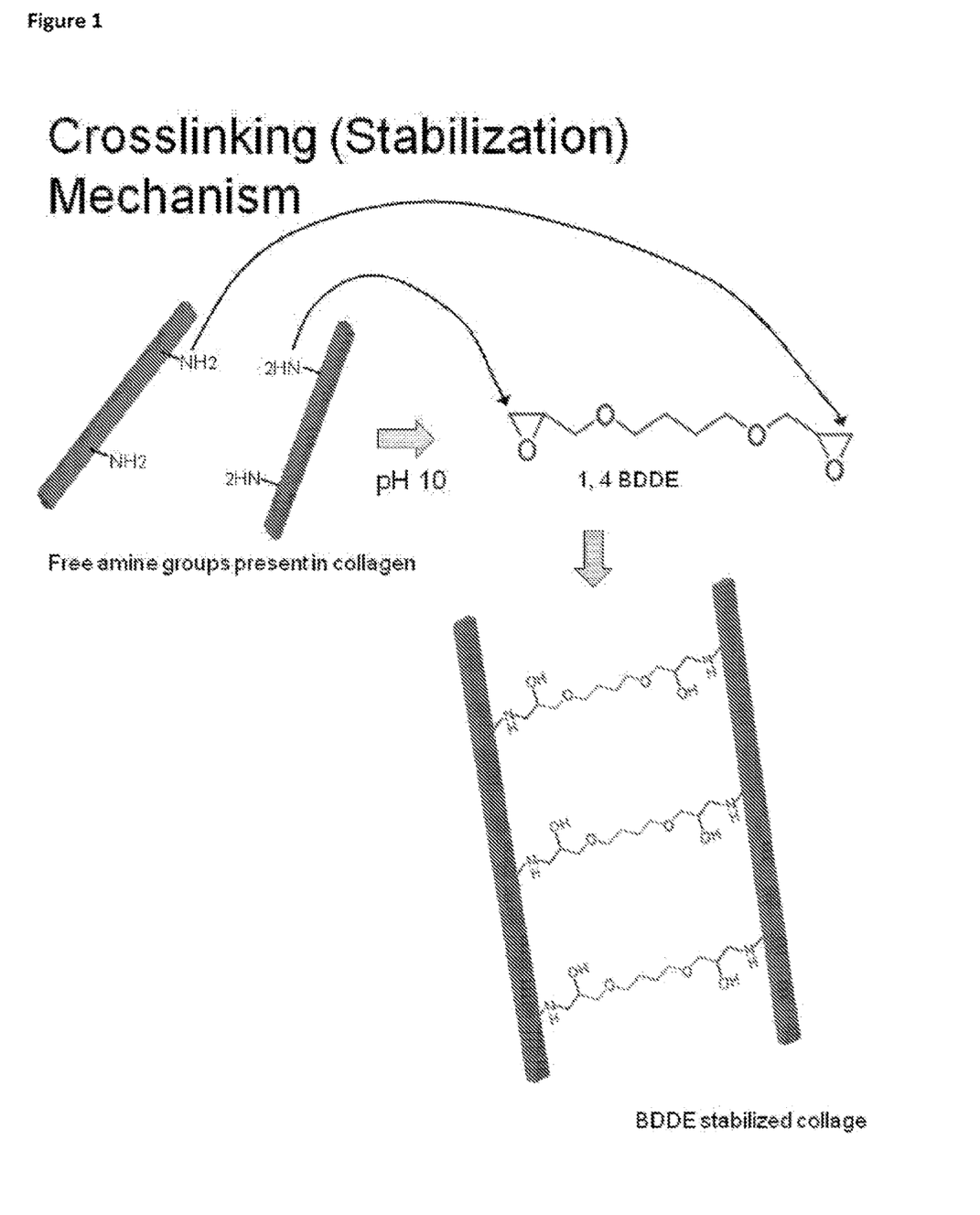
FIG. 1 depicts an exemplary crosslinking mechanism according to some embodiments of the present invention.

In one aspect, the soft tissue graft may be crosslinked by forming a covalent bond. In some embodiments, a graft having the covalent bond has a decreased hydrolysis compared to a graft without the covalent bond. In another aspect, the soft tissue graft may be crosslinked by a linker. In some embodiments, the linkers include, but are not limited to, di-epoxide or bisepoxide. In another aspect, di-epoxide or bisepoxide possesses two reactive epoxide groups capable of reacting with a number of functional groups depending on the pH of the reaction. In some embodiments, the di-epoxide is 1, 4 butanediol diglycidyl ether (BDDE), which may react in a buffer with a pH of 10. In other embodiments, other di-epoxide molecules may be used (e.g. 1,2,7,8 diepoxyoctane). For example, at a pH greater than 8, the epoxide groups of BDDE may react with amine groups present in the dermal scaffold creating a BDDE bridge or link. Once reacted, the epoxide groups may disappear and instead have "opened" to form a stable secondary amine bond as shown in FIG. 1. Also as shown in FIG. 1, an acellular human dermal scaffold can be provided with flexible bridges or links described herein. These bridges or links may function to prevent enzymatic degradation of the acellular human dermal scaffold allowing for a longer lasting graft in the presence of native collagenases and other general proteases. This type of flexible bridge or link may be contrasted with direct or zero-length links in that the flexible bridge or link (at the proper concentration of links) may provide greater enzymatic resistance while not inhibiting cellular infiltration into the scaffold.

In one aspect, the grafts that are being crosslinked and stabilized in this invention may be a dermis of human origin that is naturally more biocompatible in the human body than dermis (or other tissues) of animal origin. In another aspect, the soft tissue graft herein may be selected from a group consisting of dermis, fascia lata, tendon, ligament, blood vessel, muscle, pericardium, amniotic membrane, chorionic membrane, and submucosal subintestine. In another aspect, the soft tissue graft is a xenograft, allograft or autograft.

The invention also relates to methods of preparing a crosslinked soft tissue graft. In some embodiments, the methods of preparing a crosslinked soft tissue graft comprise selecting a soft tissue graft, optionally decellularizing said soft tissue graft, incubating the soft tissue graft with the crosslinking agent, removing the crosslinking agent after the incubation period, optionally rinsing the crosslinked soft tissue in a buffer without the crosslinking agent, optionally treating the cross-linked soft tissue graft with a plasticizer, optionally packaging the cross-linked soft tissue graft, and optionally sterilizing the crosslinked soft tissue graft.

The process for decellularizing a soft tissue graft is described in U.S. Pat. No. 6,734,018, which is incorporated by reference in its entirety herein.

Figure 2:
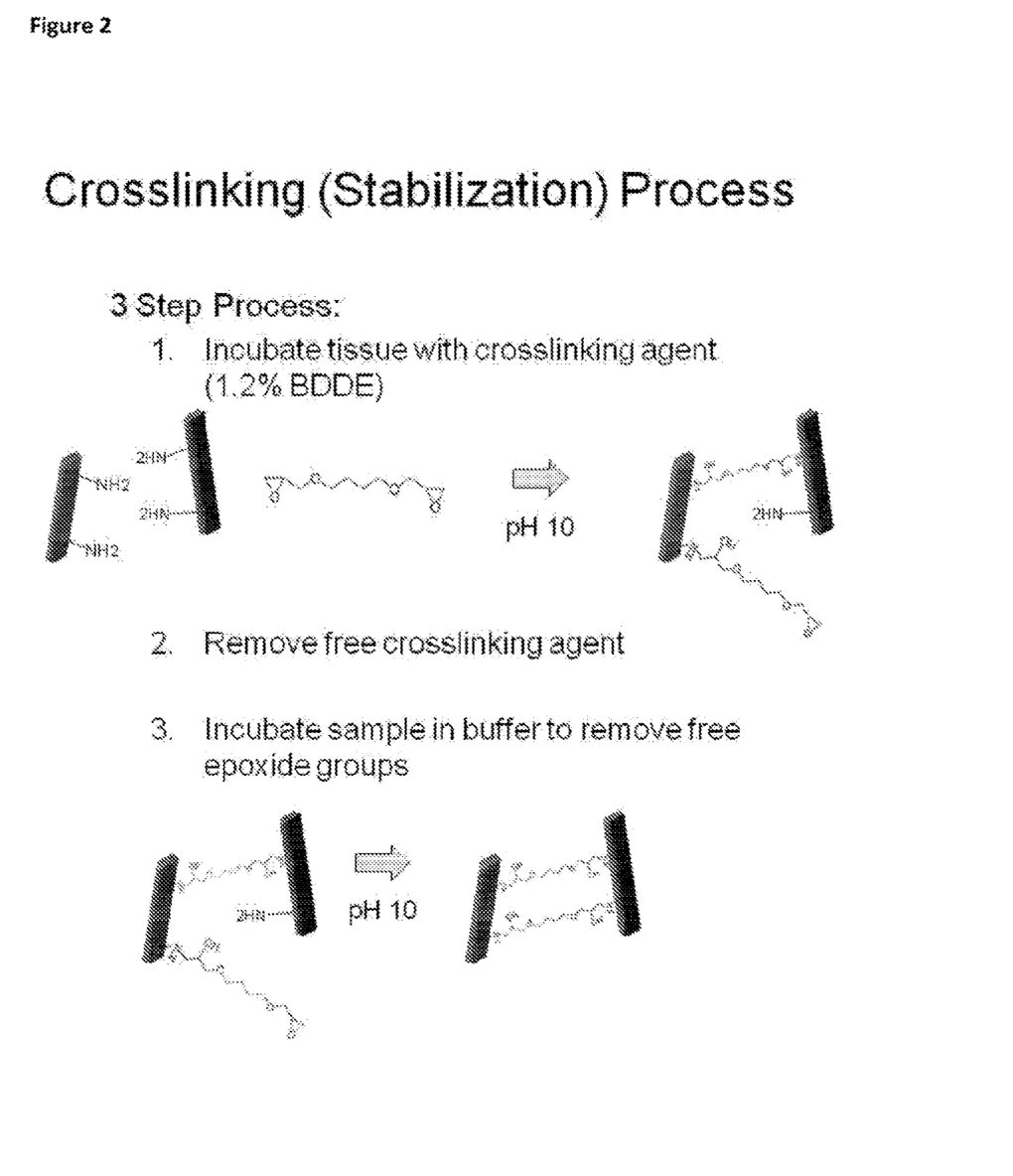
FIG. 2 depicts an exemplary crosslinking process according to some embodiments of the present invention.
Figure 3:
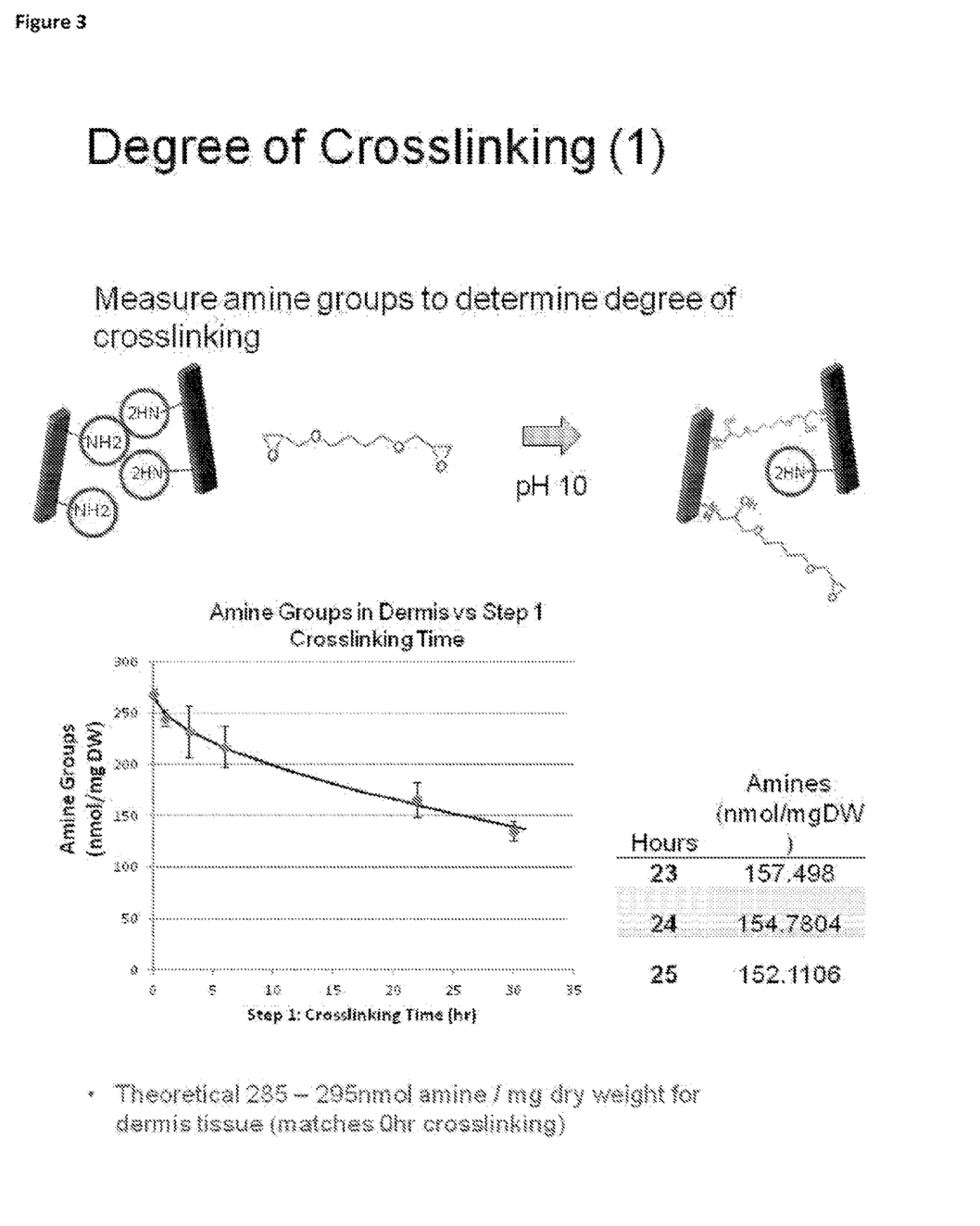
FIG. 3 depicts degree of crosslinking depending on the duration of crosslinking.

In some embodiments, the incubating step comprises mixing a linker and the soft tissue graft (e.g. an acellular human dermis) in a buffer. The buffer may have a pH of about 12, 11, 10, 9, or 8. Each of the incubating period and/or rinsing period described herein may be about 3 hours, 5 hours, 10 hours, 15 hours, 20 hours, 1 day, 2 days, 3 days, 4 days, 5 days, 6 days, or 7 days. Exemplary methods of preparing the crosslinked soft tissue graft herein are shown in FIGS. 2 and 3.

In some embodiments, the methods of preparing a crosslinked soft tissue graft may comprise incubating the soft tissue graft with the crosslinking agent (e.g. BDDE) in the range from about 1.1 to about 1.2 w/w %, from about 0.5 to about 5 w/w %, from about 0.6 to about 4 w/w %, from about 0.7 to about 3 w/w %, from about 0.8 to about 2 w/w %, or from about 1 to about 2 w/w %. In some embodiments, the methods of preparing a crosslinked soft tissue graft may comprise incubating the soft tissue graft with the crosslinking agent (e.g. BDDE) in a concentration at about 0.9 w/w %, about 1.1 w/w %, about 1.3 w/w %, about 1.5 w/w %, about 1.7 w/w %, about 1.9 w/w %, about 2.2 w/w %, about 2.5 w/w %, about 3.5 w/w %, about 4.5 w/w %, about 5.5 w/w % or less. In some embodiments, the methods of preparing a crosslinked soft tissue graft may comprise incubating the soft tissue graft with the crosslinking agent (e.g. BDDE) in a concentration at about 0.7 w/w %, about 1.0 w/w %, about 1.4 w/w %, about 1.6 w/w %, about 1.87 w/w %, about 2.0 w/w %, about 2.3 w/w %, about 2.7 w/w %, about 3.7 w/w %, about 4.7 w/w %, about 5.7 w/w % or more.

While there is a preference for freely suspended BDDE to react with a scaffold rather than the second end of an attached BDDE molecule, and the methods described herein may accelerate the process of creating a stabilized graft (e.g. without waiting a full seven days or longer).

Figure 4:
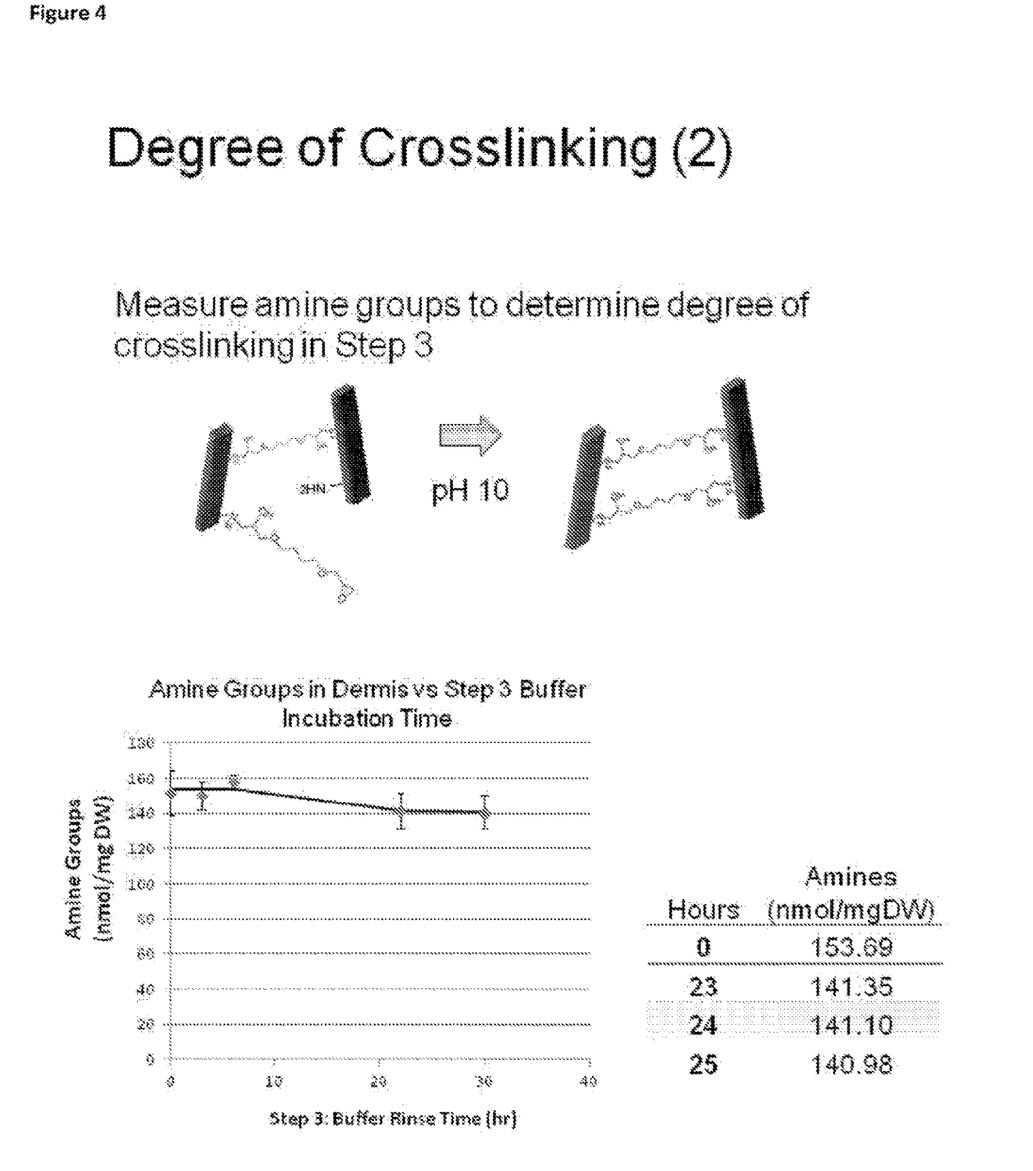
FIG. 4 depicts degree of crosslinking depending on the buffer rinse time.
Figure 5:
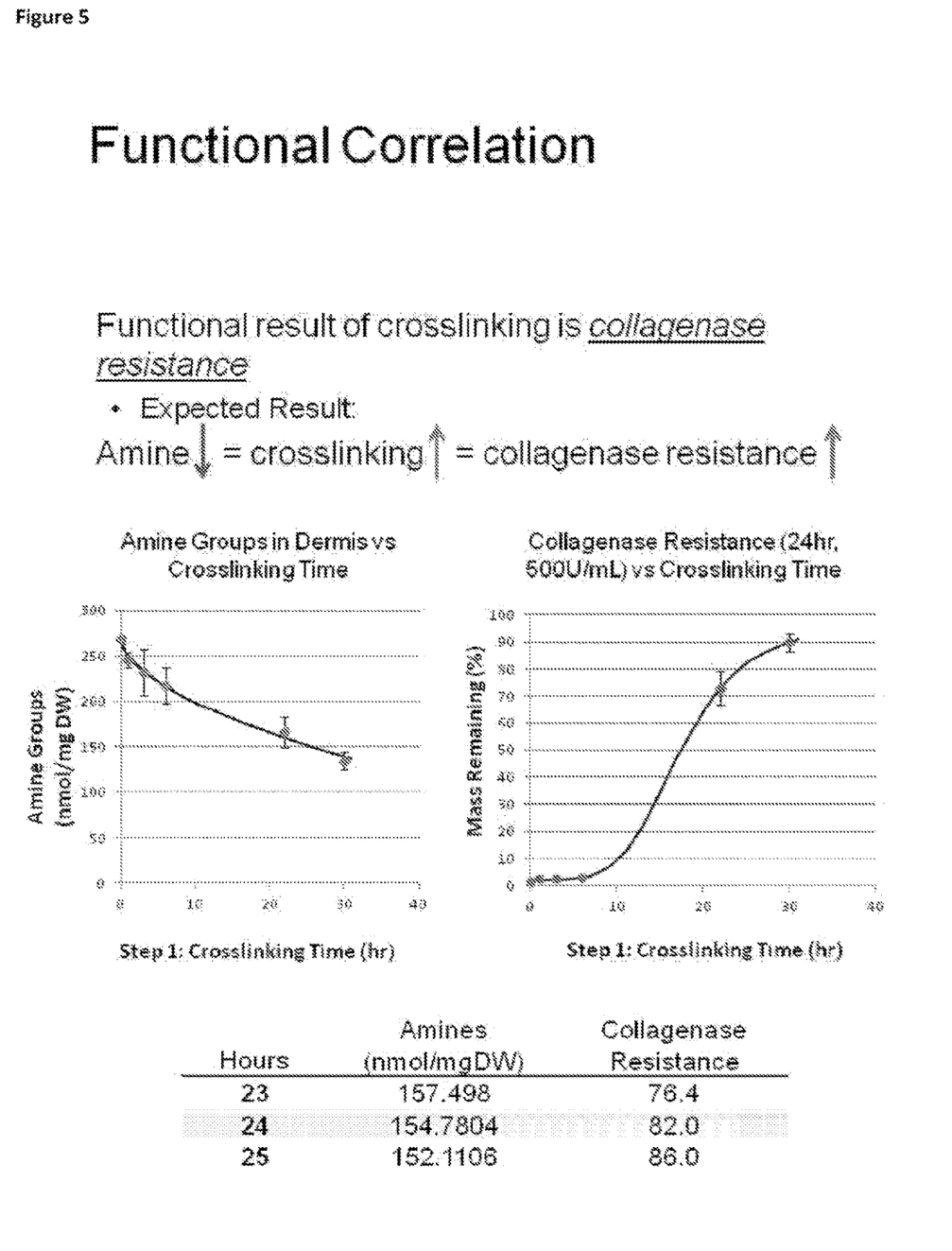
FIG. 5 depicts degree of crosslinking and collagenase resistance depending on the crosslinking time.
Figure 6A:
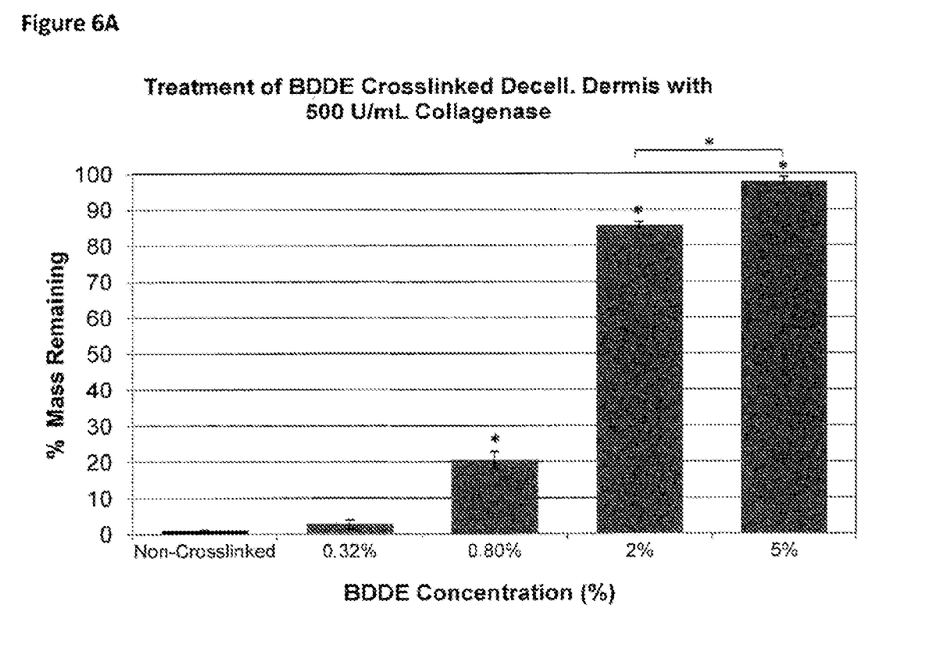
FIGS. 6A and 6B depict resistance to collagenase treatment depending on the BDDE concentration used in crosslinking.
Figure 6B:
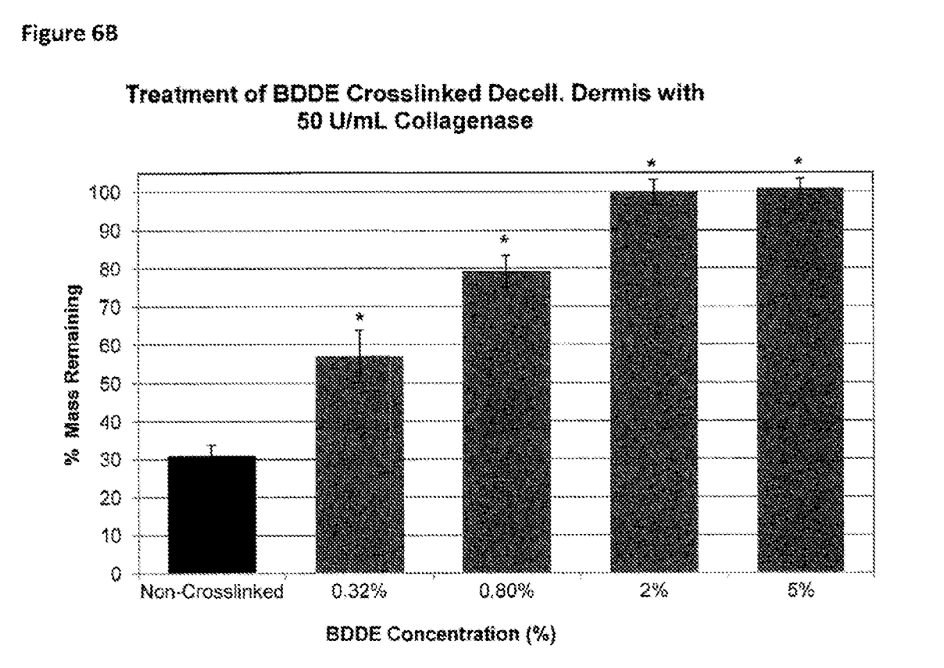
Figure 7:
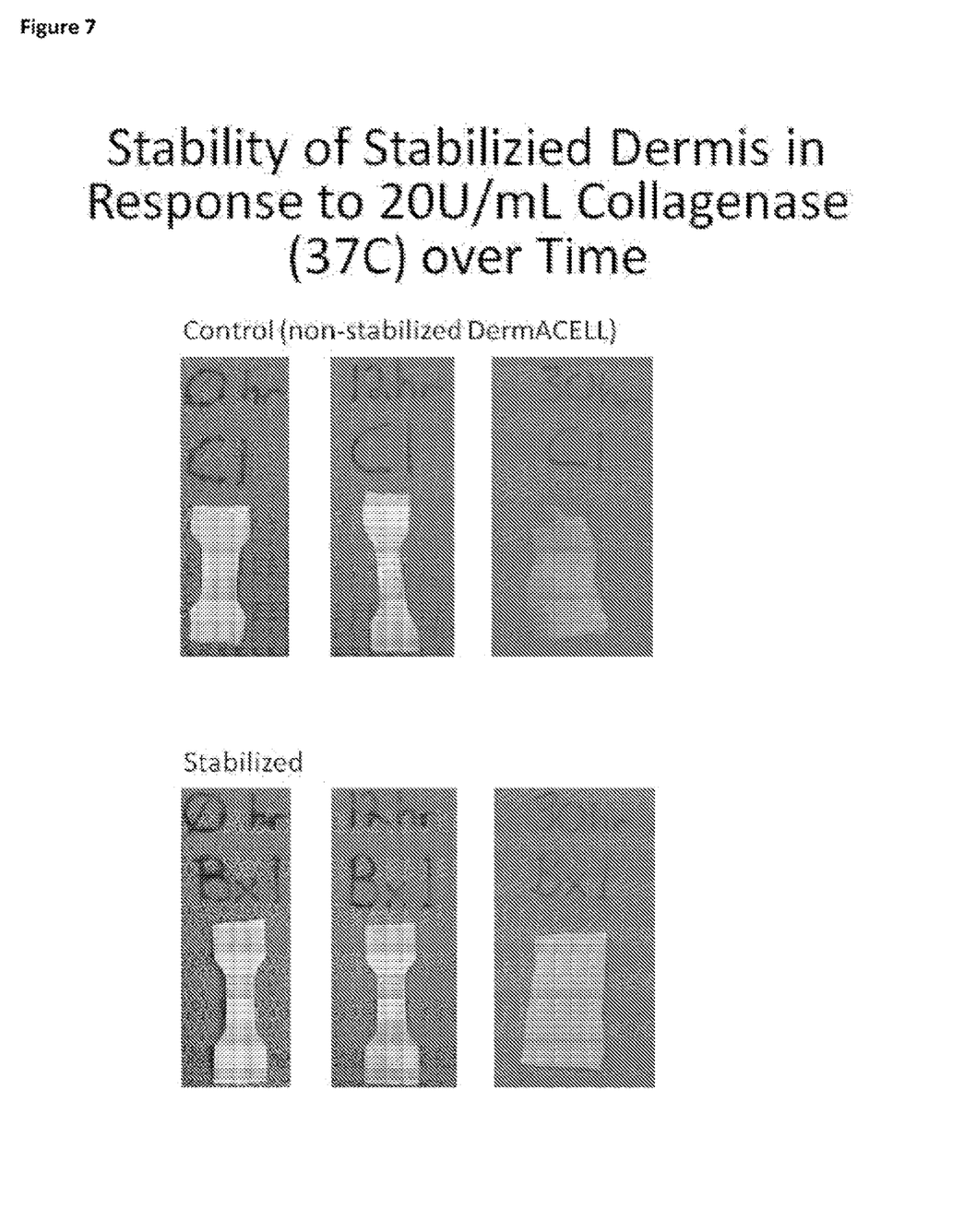
FIGS. 7 and 8 depict stability of crosslinked soft tissue graft.
Figure 8:
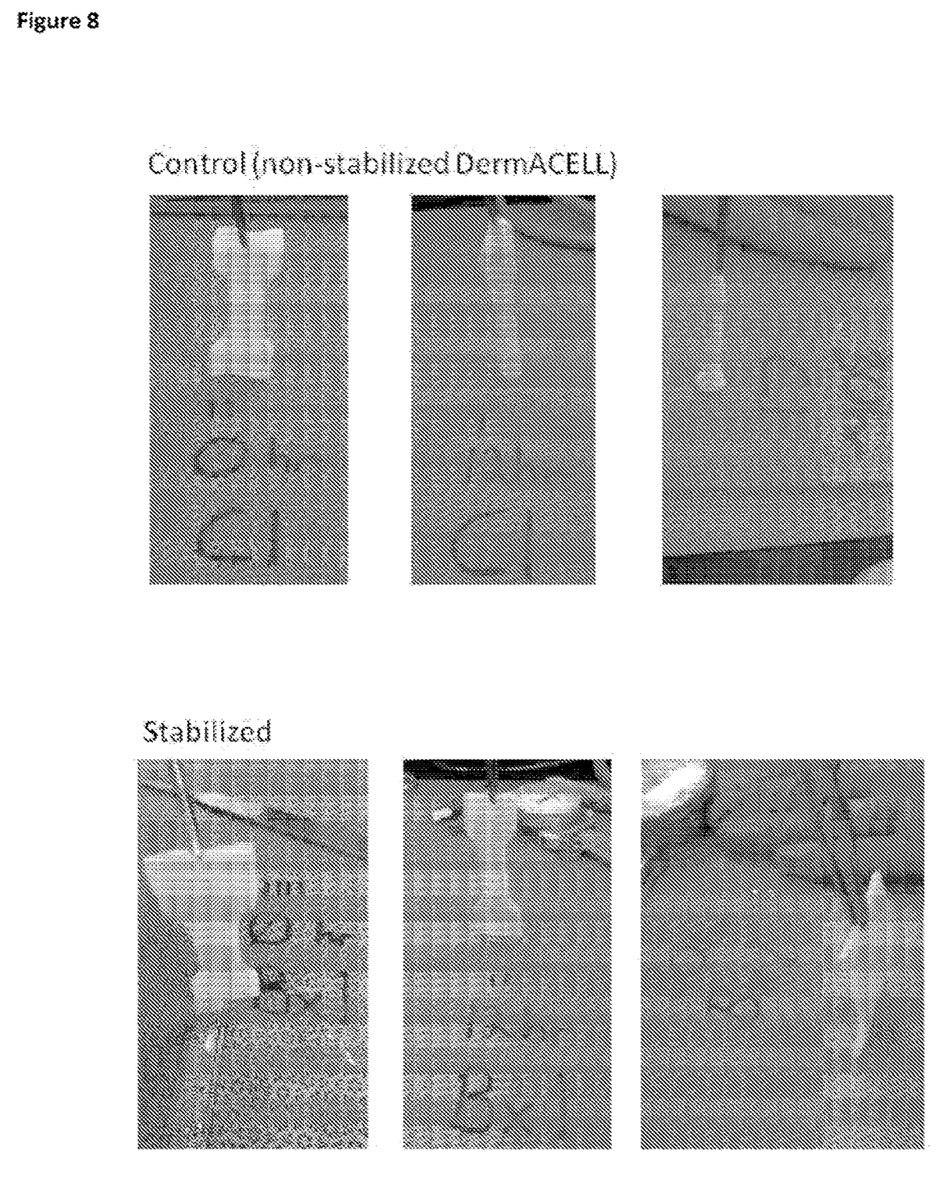
Figure 9A:
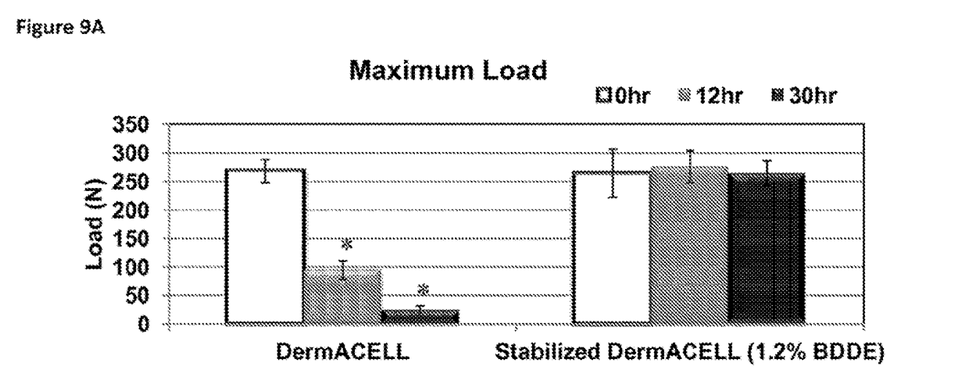
FIGS. 9A, 9B, and 9C depict strength test results of the crosslinked soft tissue graft.
Figure 9B:
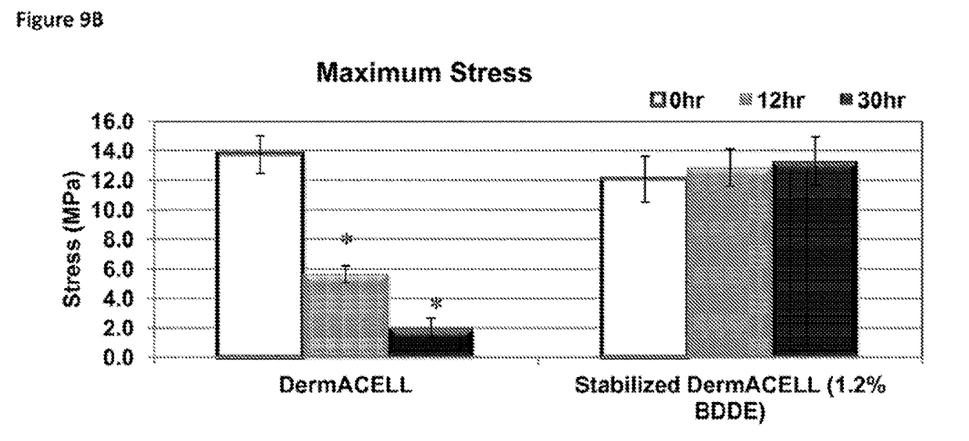
Figure 9C:
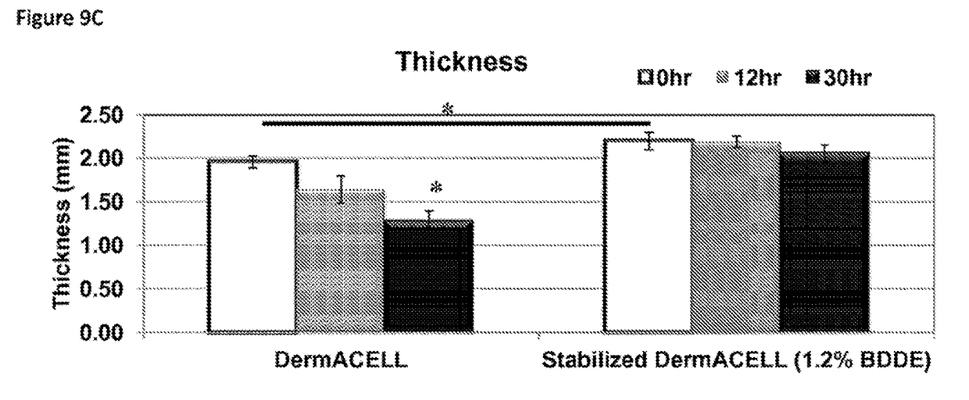
Figure 10A:
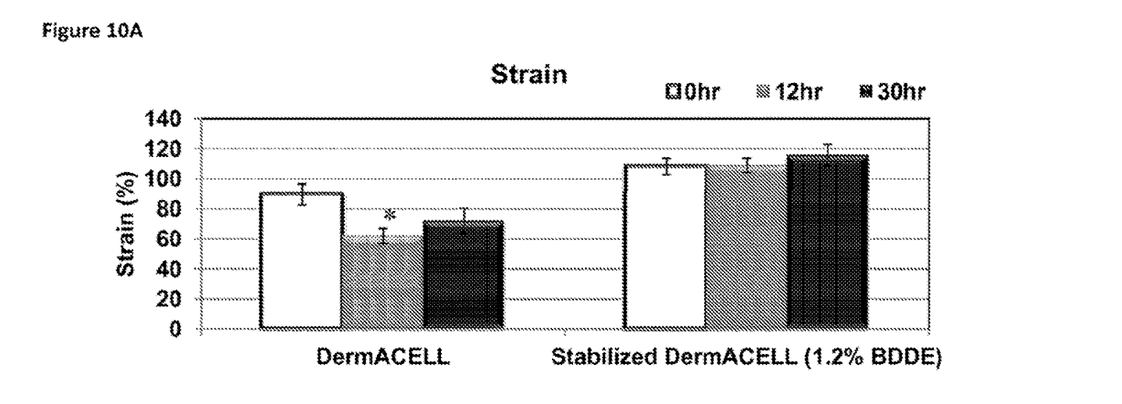
FIGS. 10A, 10B, and 10C depict strain test results of the crosslinked soft tissue graft.
Figure 10B:
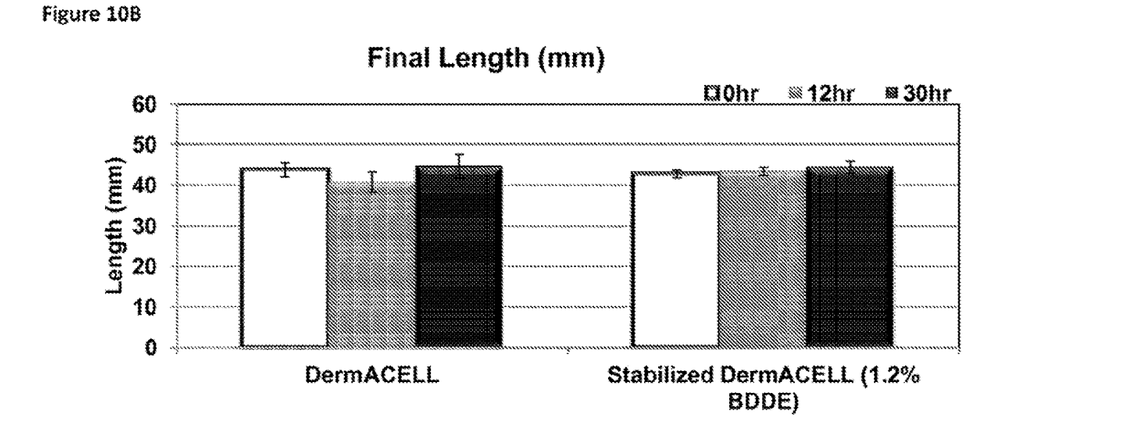
Figure 10C:
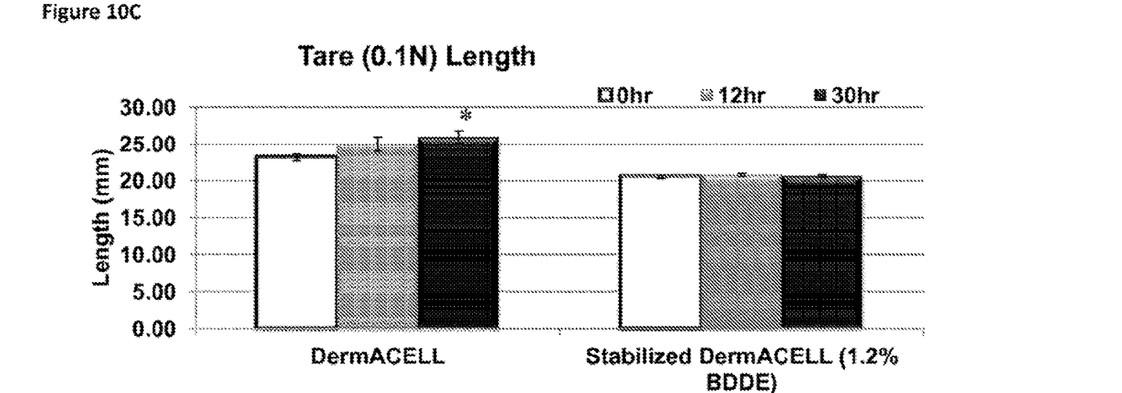
Figure 11A:
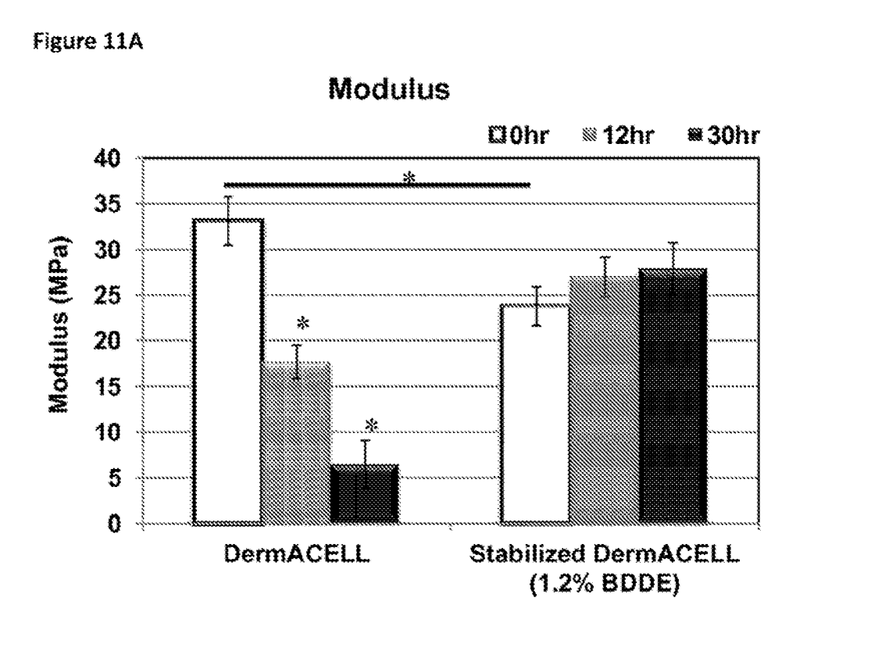
FIGS. 11A and 11B depict modulus and stiffness of the crosslinked soft tissue graft.
Figure 11B:
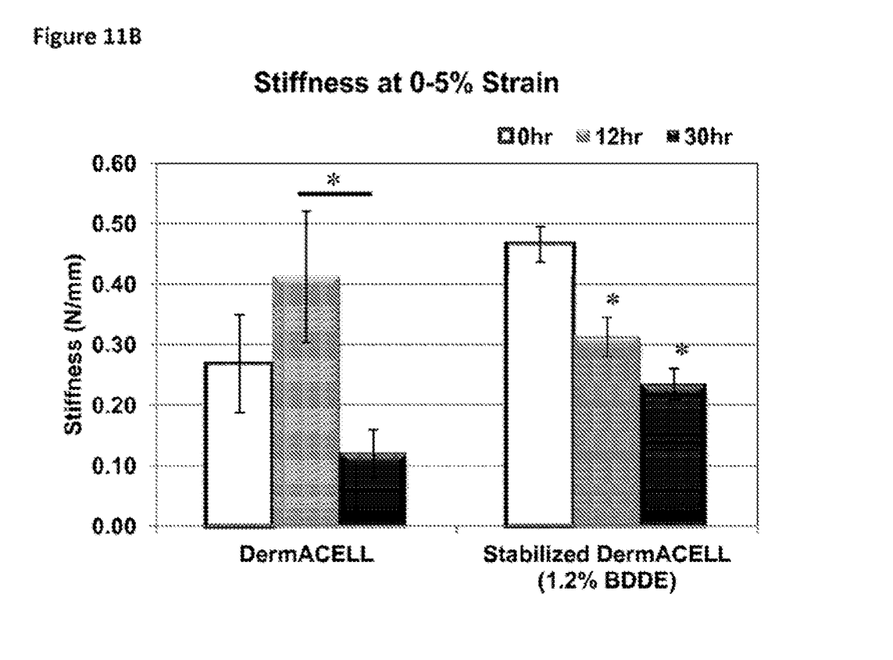
Figure 12A:
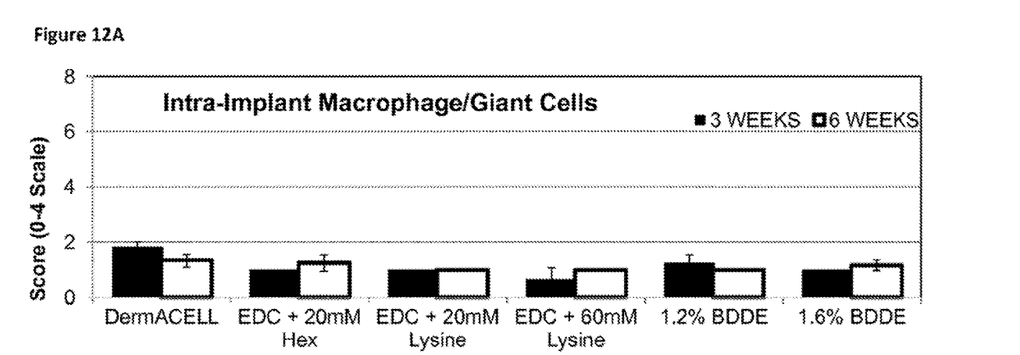
FIGS. 12A, 12B and 12C depict inflammatory response results from rat abdominal onlay model study.
Figure 12B:
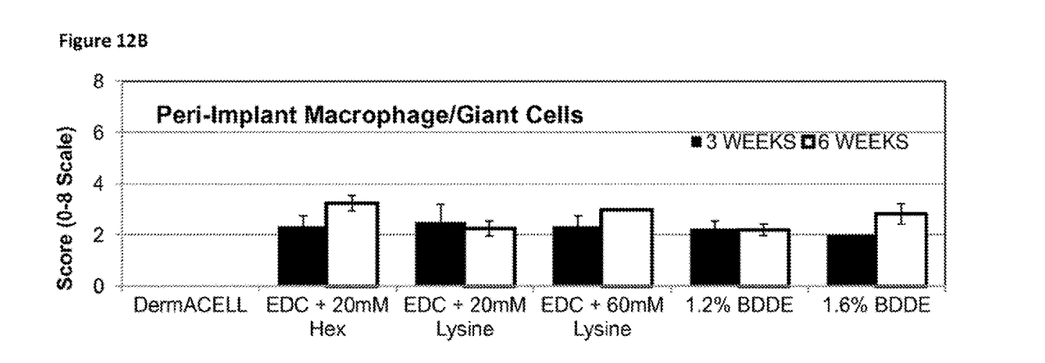
Figure 12C:
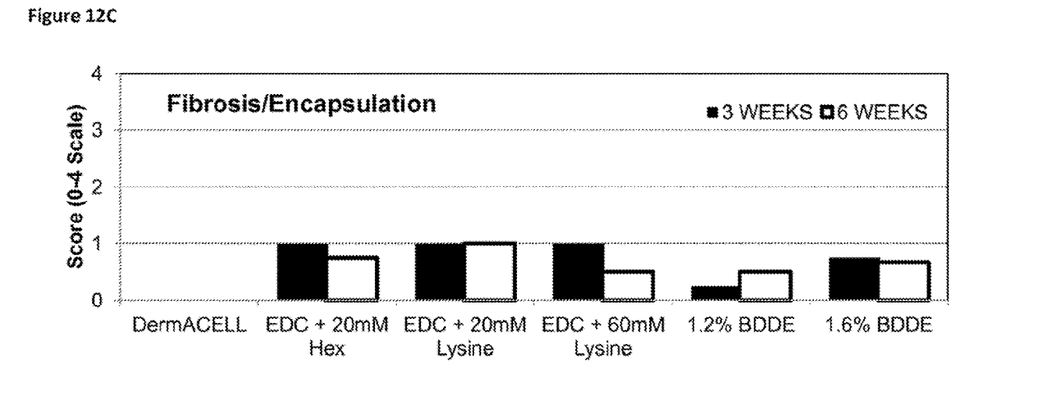
Figure 12D:
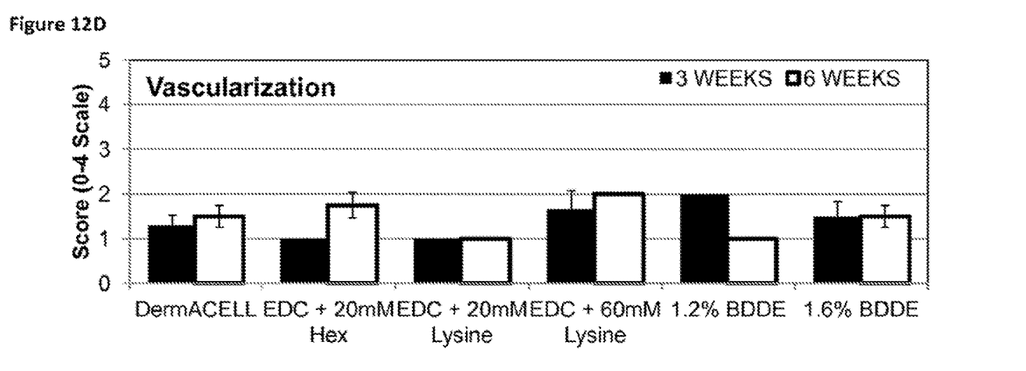
FIGS. 12D and 12E depict cellular response results from rat abdominal onlay model study.
Figure 12E:
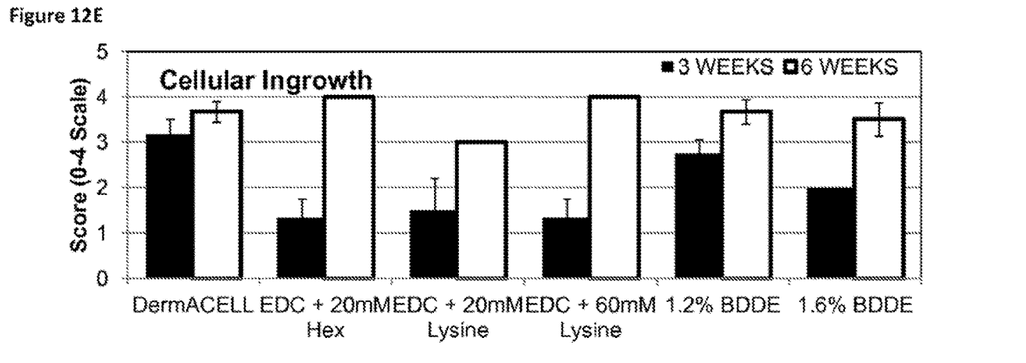

In one aspect, the crosslinks described herein may provide collagenase resistance to an acellular dermal scaffold that does not possess natural collagenase resistance. The increase in collagenase resistance may be proportional to the number of crosslinks (concentration of BDDE) introduced into the dermal scaffold (FIG. 4). The crosslinks may also provide enzymatic resistance over time (FIG. 5).

The invention also relates to methods of repairing a soft tissue defect. In some embodiments, the methods of repairing a soft tissue defect comprise obtaining a crosslinked soft tissue graft as described herein, and implanting the crosslinked soft tissue graft into the soft tissue defect site of a subject in need thereof. The method may further comprise culturing cells on the grafts prior to the implanting. Alternatively, the method may comprise seeding cells on the grafts prior to the implanting without culturing of the cells on the graft. Alternatively, the method may comprise seeding cells on the grafts prior to the implanting without any culturing of the cells. In one aspect, the additional cells may include tenocytes, fibroblasts, endothelial and/or stem cells. In some embodiments, the crosslinked soft tissue graft is sutured under tension.

The grafts according to some embodiments of the present invention may be used as an implant. An "implant" refers to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. In some embodiments, the soft tissue defect may include, but is not limited to, hernia repair, rotator cuff repair, breast reconstruction, urinary tract sling, tendon and ligament repair, chronic wound repair, and amputation stump coverage.

In one aspect, the grafts described herein can be used as a hernia repair device to provide strength to weakened abdominal tissue. Traditional acellular human dermal implants may tend to stretch and fail over time because they are slowly digested by the patient. Enzyme-resistant animal-derived tissues lack the biocompatibility and soft texture of human dermis. The grafts described herein may add enzymatic resistance to a human derived dermal graft to achieve a new soft tissue repair implant that will resist stretching and failure over time, while retaining the biocompatibility and soft texture of human dermis.

Example 1

One exemplary graft was an acellular human dermis-derived scaffold created as described by LifeNet Health U.S. Pat. No. 6,743,574, which is incorporated herein by reference, that was further treated with 1.2% BDDE in a bicarbonate buffer of pH 10. Samples were created in a two step procedure as shown in FIG. 2. First, the acellular dermal graft was incubated in a bicarbonate solution, pH 10, containing 1.2% BDDE and agitated for 24 hours. This allowed for one end of each BDDE molecule to attach to the scaffold. Then the graft was briefly rinsed in pure bicarbonate buffer, pH 10, to remove non-reacted (free) BDDE, and transferred to another container containing pure bicarbonate buffer, pH 10, for an additional 24 hours of agitation. The second 24 hours allowed for any unreacted epoxide ends present in the dermal scaffold to attach to the scaffold creating the desired scaffold crosslink. Finally, the graft was rinsed three times in saline to remove any potential remaining free BDDE and reduce the pH of the final graft material back to a physiological level.

Example 2

In a rat subcutaneous implantation, a 5% BDDE acellular human dermal scaffold was more inflammatory and less integrated than non-crosslinked acellular human dermal scaffold. Subsequently in a rat abdominal subcutaneous model, a 1.2% BDDE crosslinked human dermis displayed no apparent differences in inflammatory response or integration compared to the non-crosslinked acellular human dermal scaffold. The rat abdominal only model study results are shown in FIG. 12A-12E. A 1.6% BDDE crosslinked human dermis resulted in slightly greater inflammation and slightly lower cellular infiltration at the 3 week time point compared to the 1.2% BDDE sample, but neither comparison reached statistical significance due to the low number of replicates utilized in the screening study.

Example 3

After 24 hours of exposure to a 500 U/mL collagenase solution at 37° C., human dermis may be near completely digested (<2% mass remaining intact). The crosslinked human dermis may range from near 100% enzymatic resistance with a 5 w/w % crosslinking agent treatment down to <5 w/w % resistance with 0.32 w/w % crosslinking agent treatment. In some embodiments, the methods of preparing a crosslinked soft tissue graft may comprise incubating the soft tissue graft with the crosslinking agent (e.g. BDDE) in the range of 1.1-1.2 w/w %. A 1.2 w/w % crosslinking agent treatment was found to result in a 65-85 w/w % collagenase resistance level (depending on the donor) and acceptable biocompatibility as described herein. The increase in collagenase resistance was proportional to the number of crosslinks (concentration of BDDE) introduced into the dermal scaffold (FIG. 4).

Example 4

Exposure to a low 20 U/mL collagenase at 37° C. for 0, 12 and 30 hr demonstrated that the soft tissue graft crosslinked with the 1.2 w/w % crosslinking agent treatment retained strength and strain properties while a non-crosslinked sample of dermis did not (FIG. 5). This is relevant for the function of this invention as a hernia repair device where current non-stabilized human dermal grafts degrade over time eventually stretching and failing.

The BDDE crosslinked scaffolds had an ability to retain water better than non-crosslinked scaffolds. This was observed when samples were left out at room temperature following mechanical testing. After being exposed to the environment for 15 minutes, non-modified acellular human dermis samples were dried out and exhibited a leather-like appearance and feel. However, the BDDE crosslinked scaffolds appeared fully hydrated for at least 1 hour following the biomechanical testing. This was not seen in acellular human dermis crosslinked with another type of linker, such as lysine, that was introduced by EDC/sNHS chemistry.

The invention claimed is:

1. A method of preparing a sterilized crosslinked soft tissue graft, comprising:
   (i) selecting a soft tissue graft,
   (ii) decellularizing the soft tissue graft,
   (iii) incubating the soft tissue graft with a crosslinking agent to produce biocompatible secondary amine bonds and a crosslinked soft tissue graft, wherein production of the biocompatible secondary amine bonds is the sole crosslinking step in the process,
   (iv) removing the crosslinking agent after the incubation period,
   (v) rinsing the crosslinked soft tissue graft in a buffer without the crosslinking agent,
   (vi) packaging the crosslinked soft tissue graft, and
   (vii) sterilizing the crosslinked soft tissue graft.

2. The method of claim 1, wherein the crosslinked soft tissue graft is resistant to enzymatic degradation and capable of maintaining cell infiltration.

3. The method of claim 1, wherein the crosslinked soft tissue graft has a degree of crosslinking of about 10% to about 40%.

4. The method of claim 1, wherein the crosslinking is conducted at a pH of 8 to 12.

5. The method of claim 1, wherein the soft tissue graft is dermal, tendon or ligament tissue.

6. The method of claim 1, wherein the crosslinked soft tissue graft has a degree of crosslinking of about 10% to about 60%.

7. The method of claim 1, wherein the crosslinked soft tissue graft has a degree of crosslinking is of about 10% to about 35%.

8. The method of claim 1, wherein the crosslinked soft tissue graft has a degree of crosslinking is fromof about 10% to about 30%.

9. The method of claim 1, wherein the crosslinked soft tissue graft has a degree of crosslinking is fromof about 20% to about 40%.

10. The method of claim 1, where in the crosslinking agent comprises a diepoxide or a bisepoxide linker.

11. The method of claim 10, wherein the linker is 1,4 butanediol diglycidyl ether.

12. The method of claim 10, wherein the linker is 1,2,7,8 diepoxyoctane.

13. The method of claim 1, wherein the soft tissue graft is selected from a group consisting of dermis, fascia lata, tendon, ligament, blood vessel, muscle, pericardium, amniotic membrane, chorionic membrane, and submucosal sub-intestine.

14. The method of claim 1, wherein the soft tissue graft comprises dermal tissue.

15. The method of claim 1, wherein the soft tissue graft comprises human dermal tissue.

16. The method of claim 1, wherein the soft tissue graft comprises tendon tissue.

17. The method of claim 1, wherein the soft tissue graft comprises ligament tissue.

18. The method of claim 1, wherein the soft tissue graft is human tissue.

19. The method of claim 1, wherein the soft tissue graft is resistant to collagenase.

20. The method of claim 1, further comprising treating the crosslinked soft tissue graft with a plasticizer.

\* \* \* \* \*